United States Patent [19]

Koyama et al.

[11] Patent Number: 5,622,935
[45] Date of Patent: Apr. 22, 1997

[54] MEDICINE FOR PREVENTING AND CURING BONE FRACTURE

[75] Inventors: Masayoshi Koyama, Kawagoe; Mikiko Takahashi, Hasuda; Kazuyuki Doi, Musashimurayama, all of Japan

[73] Assignee: Hoechst Japan Limited, Tokyo, Japan

[21] Appl. No.: 335,411

[22] Filed: Nov. 3, 1994

[30] Foreign Application Priority Data

Nov. 5, 1993 [JP] Japan ................................ 5-276473

[51] Int. Cl.$^6$ .................................................. A61K 38/00
[52] U.S. Cl. .................................................. 514/21; 514/12
[58] Field of Search ........................................ 514/21, 12

[56] References Cited

U.S. PATENT DOCUMENTS 5,304,542  4/1994  Tatakis .............................. 514/12

FOREIGN PATENT DOCUMENTS

WO92/09301  6/1992  WIPO.

OTHER PUBLICATIONS

Inoue, T., Mebio, Special Version, pp. 22–27 (1990).
Horton, J.E. et al., Biochem Biophys. Acta, vol. 630: 459–462 (1980).
Takakis, D.N., Biochem. Biophys. Res. Commun., vol. 187: 287–293 (1992).
Hermodson, M. et al., J. Biol. Chem., vol. 252 (18): 6276–6278 (1977).
Ciaglowski, R.E. et al, Arch. Biochem, Biophys., vol 250: 249–256 (1986).
Ginsberg, M.H. et al., Blood, vol. 55 (4): 661–668 (1980).
Ryo, R. et al., Thromb. Res., vol. 17 (5): 645–652 (1980).
Noda, M. BIOmedica, vol. 8 (1): 28–33 (1993).
Pfeilschifter, J. et al., Endocrinology, vol. 121 (1): 212–218 (1987).
Rodan, G.A. et al., Calcium Regulating Hormones and Bone Metabolism, Elsevier Science Publishers B.V.: 183–196 (1992).

*Primary Examiner*—Paul J. Killos
*Attorney, Agent, or Firm*—Finnegan, Henderson, Farabow, Garrett & Dunner, L.L.P.

[57] ABSTRACT

Pharmaceutical composition for preventing or treating bone fracture comprising as an active ingredient a platelet factor 4.

The present composition can promote differentiation of osteoblasts so that they are effective for prophylaxis and treatment of such diseases requiring bone differentiation and proliferation as bone fracture and the like.

1 Claim, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 88 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa represents either Pyro-Gln or Glu"

( i x ) FEATURE:
        ( A ) NAME/KEY: Peptide
        ( B ) LOCATION: 20
        ( D ) OTHER INFORMATION: /note= "Xaa represents either Asp or Ser"

( i x ) FEATURE:
        ( A ) NAME/KEY: Peptide
        ( B ) LOCATION: 49
        ( D ) OTHER INFORMATION: /note= "Xaa represents either Thr or Leu"

( i x ) FEATURE:
        ( A ) NAME/KEY: Peptide
        ( B ) LOCATION: 57
        ( D ) OTHER INFORMATION: /note= "Xaa represents either Leu or Ile"

( i x ) FEATURE:
        ( A ) NAME/KEY: Peptide
        ( B ) LOCATION: 72
        ( D ) OTHER INFORMATION: /note= "Xaa represents either Arg or Asn"

(xi) SEQUENCE DESCRIPTION: SEQ ID NO:1:

| Xaa | Ser | Ser | Phe | Pro | Ala | Thr | Phe | Val | Pro | Leu | Pro | Ala | Asp | Ser | Glu |
| 1 | | | | 5 | | | | | 10 | | | | | 15 | |

| Gly | Gly | Glu | Xaa | Glu | Asp | Leu | Gln | Cys | Val | Cys | Leu | Lys | Thr | Thr | Ser |
| | | | 20 | | | | | 25 | | | | | 30 | | |

| Gly | Ile | Asn | Pro | Arg | His | Ile | Ser | Ser | Leu | Glu | Val | Ile | Gly | Ala | Gly |
| | | 35 | | | | | 40 | | | | | 45 | | | |

| Xaa | His | Cys | Pro | Ser | Pro | Gln | Leu | Xaa | Ala | Thr | Lys | Lys | Thr | Gly | Arg |
| | 50 | | | | | 55 | | | | | 60 | | | | |

| Lys | Ile | Cys | Leu | Asp | Gln | Gln | Xaa | Pro | Lys | Tyr | Lys | Lys | Ile | Leu | Lys |
| 65 | | | | | 70 | | | | | 75 | | | | | 80 |

| Lys | Leu | Leu | Asp | Gly | Asp | Glu | Ser |
| | | | | 85 | | | |

(2) INFORMATION FOR SEQ ID NO:2:

(i) SEQUENCE CHARACTERISTICS:
  (A) LENGTH: 69 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:2:

| Glu | Ala | Glu | Glu | Asp | Gly | Asp | Leu | Gln | Cys | Leu | Cys | Val | Lys | Thr | Thr |
| 1 | | | | 5 | | | | | 10 | | | | | 15 | |

| Ser | Gln | Val | Arg | Pro | Arg | His | Ile | Thr | Ser | Leu | Glu | Val | Ile | Lys | Ala |
| | | | 20 | | | | | 25 | | | | | 30 | | |

| Gly | Pro | His | Cys | Pro | Thr | Ala | Gln | Leu | Ile | Ala | Thr | Leu | Lys | Asn | Gly |
| | | 35 | | | | | 40 | | | | | 45 | | | |

| Arg | Lys | Ile | Cys | Leu | Asp | Leu | Gln | Ala | Pro | Leu | Tyr | Lys | Ile | Ile | Lys |
| | 50 | | | | | 55 | | | | | 60 | | | | |

| Lys | Leu | Leu | Glu | Ser |
| 65 | | | | |

MEDICINE FOR PREVENTING AND CURING BONE FRACTURE

BACKGROUND OF THE INVENTION

1. Field of the Invention

The invention relates to pharmaceutical compositions for preventing or treating bone formation-relating diseases, particularly fractures.

2. Description of the Prior Art

Bones maintain a supporting function as endoskeleton by repeated local bone resorption and bone formation to substitute old bones with new ones and they also prepare for a rapid reactivity to various mechanical stresses and changes in mineral balance. This osteoanagenesis is performed mainly by bone resorption cells such as osteoclasts and the like and bone formation cells such as osteoblasts and the like, based upon coupling of both cells. Recently, osteoblasts have been reported not only to have the function of bone formation, but to closely relate to differentiation and activation of osteoclasts, so that there may be an increased possibility of playing a role as a controlling center in cellular bone reconstruction [Inoue, T., Mebio (1990), Special Version p. 2–7].

The plate let factor 4 (PF4) is the protein which is characteristic of platelet and may be specifically bound to heparin to neutralize the anticoagulant activity of heparin. And further, it is known that PF4 may act as a chemotactic factor on leukocytes, monocytes and fibroblasts and show an anti-collagenase activity for protecting tissues from impairment caused by the collagenase released from leukocytes (polynuclear neutrophils) in inflammatory lesions. It was also elucidated that human PF4 blocked reversibly parathyroid hormone (PTH)-stimulated $^{45}Ca^{2+}$ release from newborn rat bone in vitro [Horton, J. E., et al., Biochem. Biophys. Acta. (1980), Vol. 630, p. 459–462]. Recently, human PF4 has been found to inhibit human osteosarcoma cell lines Saos-2 and G-292 proliferation, from which the antitumor effect is expected [Tatakis, D. N., Biochem. Biophys. Res. Commun. (1992), Vol. 187, p. 287–293].

Human PF4 was found to be composed of 70 amino acids and bovine PF4 was found to be the polypeptide composed of 88 amino acids, while the respective sequences were determined [Hermodson, M., et al., J. Biol. Chem. (1977), Vol. 252, p. 6276–6278; Ciaglowski, R. E., et al., Arch. Biochem. Biophys. (1986), .Vol. 250, p. 249–256].

PF4 is released from platelets in the binding form with proteoglycan, but it is believed that proteoglycan may be replaced with heparin. Recently, there has been investigated determination of PF4 values in plasma by radioimmunoassay. PF4 activity has been abundantly detected in the fraction containing α-granules which were isolated by the intracellular organella fractionation method. And further, PF4 was detected in platelets and megakaryocytes by immunofluorescence microscopy technique, while its synthesis in megakaryocytes was assumed [Ginsberg, M. H., et al., Blood (1980), Vol. 55, p. 661–668; Ryo, R., et al., Thromb. Res. (1980), Vol. 17, p. 645–652].

On the other hand, it is known that a variety of bone formation factors may participate in the course of bone formation [Noda, M., BIOmedica (1993), Vol. 8, p. 28–33]. In particular, it is known that estrogen, PTH and anabolic hormone may promote bone formation. Although PF4 is known to inhibit bone resorption (Horton, J. E., et al., loc. cit.), no report has suggested that PF4 may be also effective in bone formation.

DETAILED DESCRIPTION OF THE INVENTION

An object of the invention is to provide a peptide which can be applied as a new therapeutic agent effective for bone formation. More specifically, there has been desired a peptide which can show a far safer bone formation-promoting effect than previously known agents such as estrogen, PTH or anabolic hormone which show strong side-effects and are required for a full observation of course with their suggested bone formation-promoting effect.

Now, the present inventors have made various studies and found that bovine PF4 and human PF4 can promote bone formation, upon which this invention has been completed.

It is believed that in blood of fetuses and the newborn of mammals including human beings various growth factors would be found, which might promote growth of various cellular tissues in remarkably growing fetuses and the newborn. Using bovine newborn serum easily available in quantities as a starting material, the present inventors attempted purification and isolation of the protein factor which may increase an alkaline phosphatase (ALPase) activity in osteoblast-like osteosarcoma cell lines.

As the osteoblast-like osteosarcoma cell lines which may be applied for the determination of ALPase promoting activity, there may be employed, for example, ROS $17/2.8$ cell lines. It is regarded as an index for bone formation that osteoblast-like osteosarcoma cell line ROS $17/2.8$ increased ALPase activity; for instance, transforming growth factor-β (TGF-β) was proved to increase ALPase activity [Pfeilschifter, J., et al., Endocrinology (1987), Vol. 121, p.212–218; Rodan, G. A., et al., Calcium regulating hormones and bone metabolism, Elsevier Science Publishers B. V., (1992), p. 183–196].

As it was known that various growth factors may be easily bound to heparin, heparin affinity column chromatography may first be employed to isolate the bound fractions. Then reverse-phase HPLC may be employed for further fractions. Each fraction was determined for its ALPase promoting activity. As a result, there was discovered the fraction capable of increasing ALPase activity in ROS $17/2.8$ cells. The fraction was determined for its partial amino acid sequence and was investigated as to whether or not it may be any known protein by referring to the protein database. As a result, the said sequence was in agreement with the well-known amino acid sequence of bovine PF4 and thus the resulting active fraction was estimated to be PF4. Accordingly, similar investigation of a commercially available purified human PF4 has confirmed its ALPase increasing activity. Thus, the said active fraction was identified to be PF4, upon which the invention has been completed.

This invention is concerned with a pharmaceutical composition for preventing or treating fractures which comprises an effective amount of PF4 in combination with a pharmaceutically acceptable carrier or excipient. This invention is also concerned with a method for preventing or treating fractures which comprises administering to a subject suffering from fractures an effective amount of PF4. This invention is further concerned with a method for the preparation of PF4 as a preventing or treating agent for fractures.

PF4 may be produced by purification from platelets, by synthesis of the DNA encoding PF4 based on any known amino acid sequence or by cloning and expression $PF^4$ gene by genetic engineering well-known to those skilled in the art.

PF4 may be used as a therapeutic or prophylactic agent for osteoblast-relating diseases. In particular, it is effective in the treatment of those diseases requiring promotion of osseous differentiation and proliferation such as fractures and so on in view of promoted differentiation of osteoblasts.

For the treatment of fractures, one may most preferably adopt an administration wherein PF4 is applied topically or directly to the affected part after blending with a suitable gel base. PF4 may otherwise be given via systemic route using its aqueous injections in view of its high water-solubility, and also given via nasal or inhalational route in the form of fine-particle aerosols.

The dose may be 1–100 μg/applied part/person/day for topical application and 0.1–10 mg/kg/day for systemic application.

This invention will be explained by way of the following examples.

EXAMPLE 1

Purification of PF4 from bovine newborn serum

1) Partial purification by heparin affinity chromatography

To 1 liter of newborn bovine serum (purchased from GIBCO Laboratories Inc.) was added 20.5 g of sodium chloride. The salted serum was developed with heparin-Toyopearl column (a diameter of 5 cm×a length of 5.5 cm, available from TOSOH CORPORATION), which had been equilibrated with Tris buffer A (20 mM Tris-HCl, pH 7.5, 0.5M NaCl), at a flow rate of 3 ml/minute. Thereafter, the column was thoroughly washed with the Tris buffer A.

After washing, the peptides or proteins adsorbed on the heparin-Toyopearl column were eluted with Tris buffer B (20 mM Tris-HCl, pH 7.5, 1.0M NaCl). The eluates were monitored with absorbance at 280 nm using a photometer and about 300 ml of the fractions having a higher absorbance.

2) Purification by reverse-phase HPLC

The eluate obtained by the above procedure 1) was developed with Cosmosil $5C_{18-300}$ column (a diameter of 4.6 mm×a length of 250 mm, available from Nakarai Tesuku K. K.), which had been equilibrated with water containing 0.1% trifluoroacetic acid (TFA), and the column was thoroughly washed with water containing 0.1% TFA. Thereafter, the peptides or proteins adsorbed were eluted with a linear gradient of 0–80% acetonitrile containing 0.1% TFA. The eluates were monitored with absorbance at 214 nm to collect every peak. The elution pattern is shown in FIG. 1.

EXAMPLE 2

Determination of ALPase promoting activity on every peak

Osteoblast-like osteosarcoma cell line ROS $17/2.8$ was planted into a 24-well culture plate at $2\times10^4$ cells/well in 1 ml of 5% newborn bovine serum-containing F12 medium and incubation was carried out in a $CO_2$ incubator at 37° C. for 3 days. Then, the culture medium was removed and the cells were washed once with the F12 medium and further incubated with 1 ml of a serum-free medium (0.2% bovine serum albumin-containing F12 medium) containing each peak fraction obtained by the procedure 2) and incubation was continued over a further 2 days. Thereafter, the culture medium was removed, the cells were washed three times with Dulbecco PBS (purchased from GIBCO Laboratories Inc.) and 200 μl of a solution containing 0.2% Nonidet P-40 and 0.9% sodium chloride were added. The resulting mixture was allowed to stand at room temperature for one hour to dissolve the cells. Subsequent centrifugation was performed using Eppendorf centrifuge for 5 minutes to collect the supernatant. To 20 μl of the supernatant was added a solution to make 10 mM p-nitrophenyl phosphate in 0.1M glycine, 1 mM $ZnCl_2$, 1 mM $MgCl_2$, pH 10.4 and, after stirring, the reaction was allowed to proceed at 37° C. for 20 minutes. The reaction was monitored by measuring absorbance at 420 nm. The results of the determination of the effect of the peak 1 as shown in FIG. 1 on the ALPase promoting activity in the ROS $17/2.8$ cells are shown in Table 1, in which dose represents a protein concentration in the peak fraction and each value for the ALPase activity represents mean±standard deviation in each group.

TABLE 1

| Added compound | Dose (μg/ml) | ALPase activity (mU*/mg whole protein) |
| --- | --- | --- |
| Control | 0 | 49.6 ± 16.8 |
| Peak 1 | 5.0 | 271.7 ± 15.1 |

*1U = released p-nitrophenol (μmol)/minute

EXAMPLE 3

Determination of physico-chemical properties of peptides in the peak 1 in FIG. 1

1) Identification by amino acid sequence analysis

The peptide in the fraction confirmed to be active in Example 2 was subjected to a usual analysis for the N-terminal sequence using an amino acid sequencer, Model 477A/120A (available from Applied Biosystems Inc.), but the sequence could not be determined. It was assumed that the N-terminus of the protein was blocked. Therefore, the active peptide was fractionated to perform the determination of its partial amino acid sequence. About 1 nM of the active peak protein (determined by amino acid analysis) was dried by a speedback concentrator (SAVANT Inc.) and dissolved in 200 μl of a solution of 6M guanidine·HCl, 0.2M Tris-HCl and 2 mM EDTA (pH 8.0). Then, 20 nmol of dithiothreitol (available from Nakarai Tesuku K. K.) was added and the reaction was allowed to proceed at 37° C. for 1.5 hours. To the reaction mixture was added 100 nmol of 4-vinylpyridine (available from Aldrich Chemical .Co., Inc.) and the reaction was further allowed to proceed at 37° C. for 1.5 hours. This reaction mixture was developed over Cosmosil $5C_{18-300}$ column (a diameter of 4.6 mm×a length of 250 mm, available from Nakarai Tesuku K. K.), which had been equilibrated with water containing 0.1% TFA, and the column was thoroughly washed with water containing 0.1% TFA. Then, the peptides or proteins adsorbed were eluted with a linear gradient of 0–80% acetonitrile containing 0.1% TFA. The eluates were monitored for absorbance at 214 nm to collect every peak, whereby there was obtained pyridine-ethylated protein.

The so obtained protein was dried by a speedback concentrator and dissolved in 500 μl of 20 mM Tris-HCl buffer, 0.1M NaCl at pH 8.5. The lysylendopeptidase (Achromobacter protease I (EC 3.4.21.50)) (available from Wako Pure Chemical Industries, Ltd.) dissolved in 20 mM Tris buffer, 0.1M NaCl at pH 8.5, was added thereto so as to bean enzyme/substrate (molar ratio) of 1/200. The reaction was allowed +to proceed at 30° C. for 16 hours to perform digestion. The solution containing the resultant peptides was separated with Cosmosil $5C_{18-300}$ column (a diameter of 4.6 mm×a length of 250 mm, available from Nakarai Tesuku K. K.) to collect the fraction at every peak. The amino acid sequence of the two fractions of those obtained was determined by an amino acid sequencer, Model 477A/120A.

The resultant amino acid sequence was searched as to whether or not there may be any identical one upon the protein database to confirm that it was bovine PF4 (Ciaglowski, R. E., et al., loc. cit. ). The resulting amino acid sequence is shown as SEQ ID No.: 1 in the Sequence Listing.

2) Analysis by electrophoresis

The molecular weight of the peptide in the peak 1 as shown in FIG. 1 was confirmed by SDS electrophoresis under reduced conditions to show an apparent molecular weight of about 11,000–14,000. This molecular weight is in agreement with the reported molecular weight for bovine PF4 (Ciaglowski, R. E., et al., loc. cit.).

EXAMPLE 4

Determination of ALPase promoting activity of human PF4

Human PF4 available from Calbiochem Inc. was purified for use. It was developed over Cosmosil $5C_{18-300}$ column (a diameter of 4.6 mm×a length of 250 mm, available from Nakarai Tesuku K. K.), which had been equilibrated with water containing 0.1% TFA, and the column was thoroughly washed with water containing 0.1% TFA. Thereafter, the peptides or proteins adsorbed were eluted with a linear gradient of 0–80% acetonitrile containing 0.1% TFA. The eluates were monitored with absorbance at 214 nm to collect the fractions at every peak. The elution pattern is shown in FIG. 2. The effect of these fractions on ALPase promoting activity in ROS $17/2.8$ cells was determined in the same manner as described in Example 2 to determine the peak 1 as the active fraction. The results by determination of the effect of the peak 1 on ALPase promoting activity in ROS $17/2.8$ cells are shown in Table 2. The amino acid sequence of human PF4 is shown as SEQ ID No.: 2,

TABLE 2

| Added compound | Dose (µg/ml) | ALPase activity (mU*/mg whole protein) |
| --- | --- | --- |
| Control | 0 | 49.6 ± 16.8 |
| Human PF4 | 0.1 | 92.2 ± 12.4 |
|  | 0.3 | 88.5 ± 23.0 |
|  | 1.0 | 139.6 ± 3.7 |
|  | 3.0 | 331.4 ± 86.9 |

*1U = released p-nitrophenol (µmol)/minute

Figure 1:
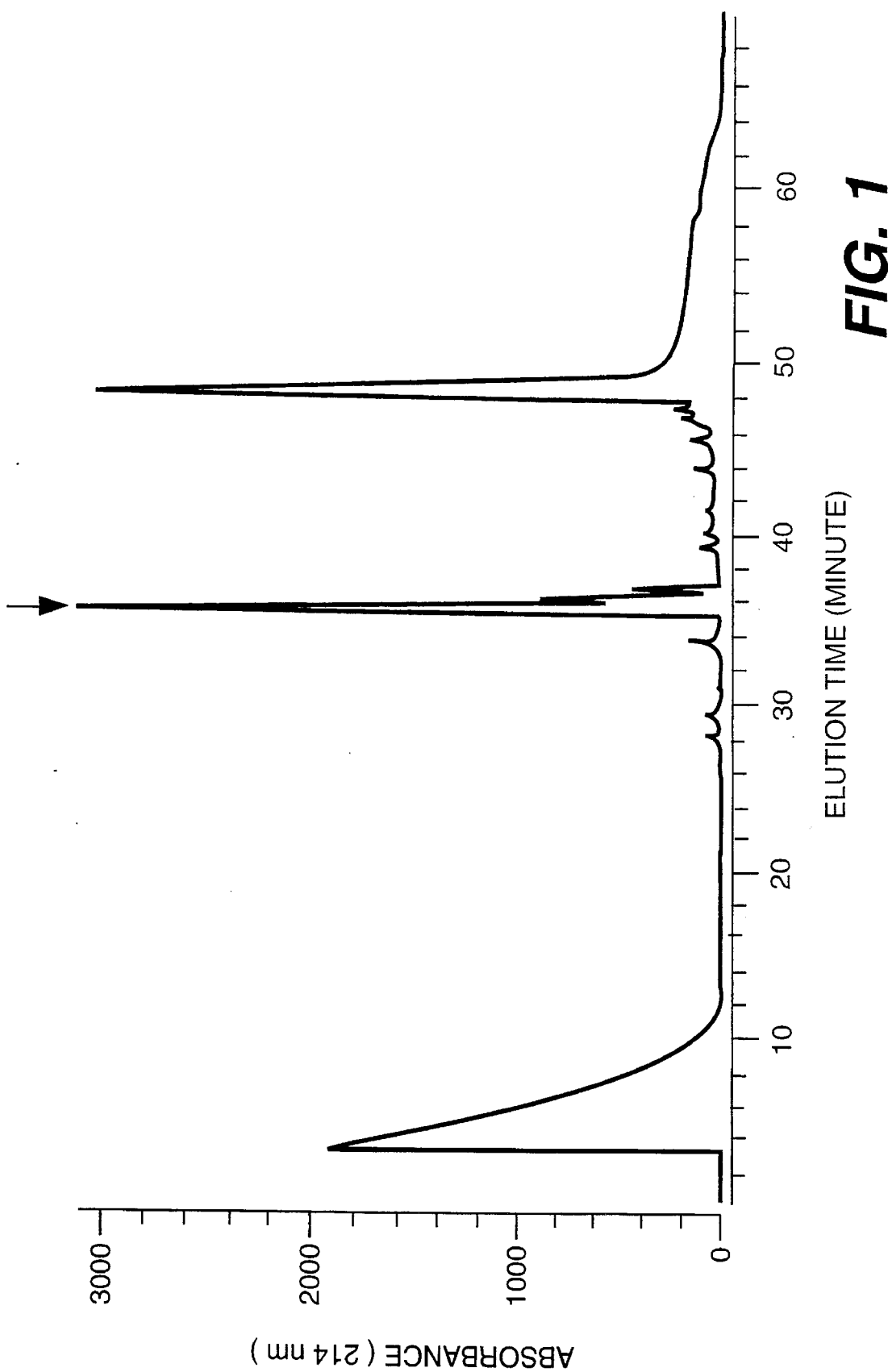
FIG. 1 shows the pattern wherein the fractions bound to heparin affinity chromatography and eluted were further developed using reverse-phase HPLC and wherein the arrow indicates the active fraction (peak 1) containing bovine PF4.
Figure 2:
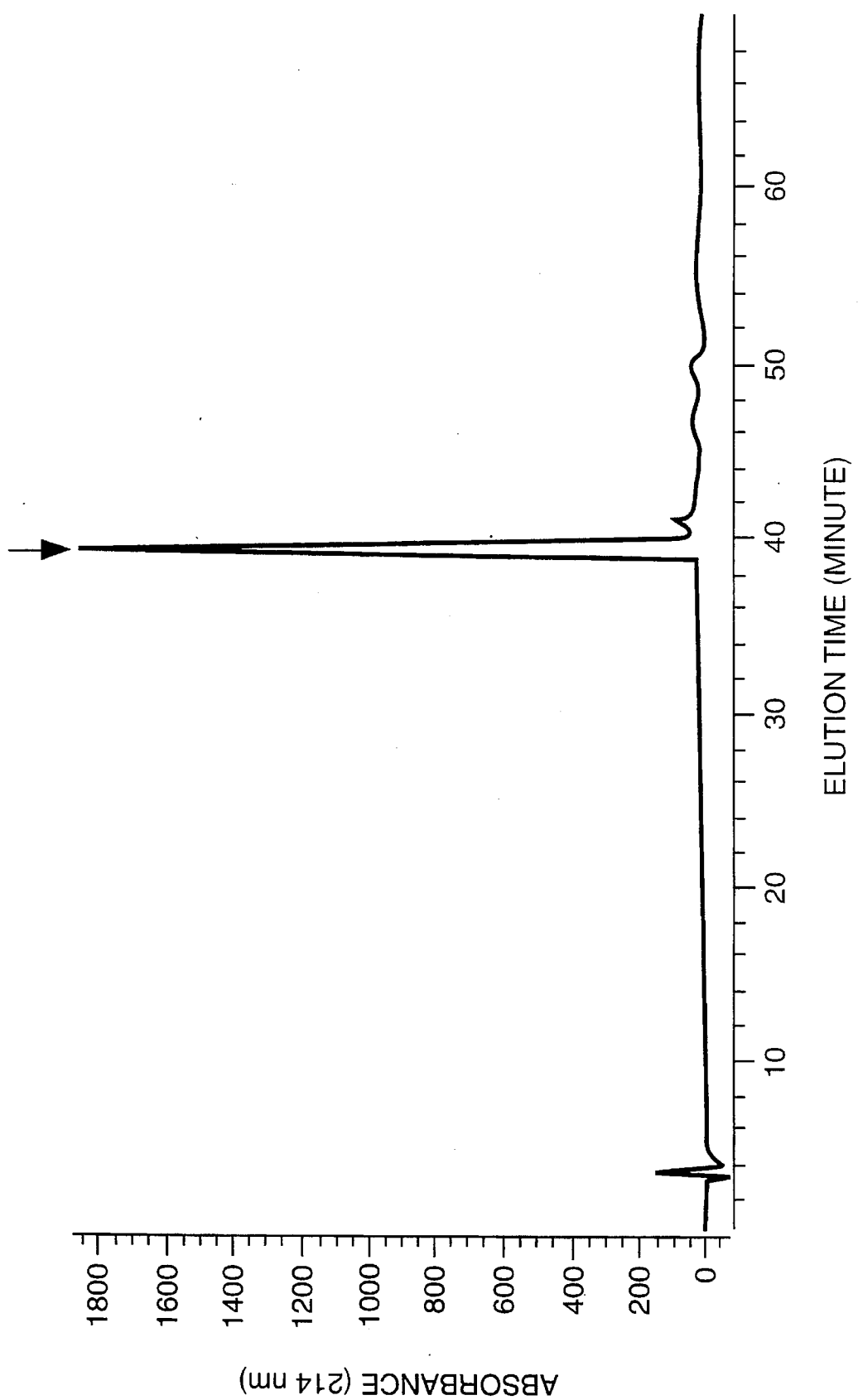
FIG. 2 shows the pattern wherein the partially purified human PF4 was developed by reverse-phase HPLC and wherein the arrow indicates the active fraction (peak 1) containing human PF4.

What is claimed is:

1. A method for preventing or treating fractures which comprises administering to a patient suffering from or prone to bone fracture resulting from osteoblast-relating disease an effective amount of purified platelet factor 4.

* * * * *